United States Patent

Ojima

[11] Patent Number: 6,100,411
[45] Date of Patent: Aug. 8, 2000

[54] TAXOID ANTI-TUMOR AGENTS AND PHARMACEUTICAL COMPOSITIONS THEREOF

[75] Inventor: Iwao Ojima, Stony Brook, N.Y.

[73] Assignee: The Research Foundation of State University of New York, Stony Brook, N.Y.

[21] Appl. No.: 08/608,003

[22] Filed: Mar. 4, 1996

Related U.S. Application Data

[63] Continuation-in-part of application No. 08/330,956, Oct. 28, 1994, abandoned.

[51] Int. Cl.⁷ ........................ C07D 305/14; A61K 31/337
[52] U.S. Cl. ........................... 549/510; 549/511; 514/449
[58] Field of Search ....................................... 549/510, 511

[56] References Cited

U.S. PATENT DOCUMENTS

| | | | |
|---|---|---|---|
| 5,229,526 | 7/1993 | Holton | 549/213 |
| 5,294,637 | 3/1994 | Chen et al. | 514/449 |
| 5,399,726 | 3/1995 | Holton et al. | 549/510 |
| 5,728,850 | 3/1998 | Holton et al. | 549/510 |
| 5,739,362 | 4/1998 | Holton et al. | 549/510 |

OTHER PUBLICATIONS

Greene et al, "Protective Groups in Organic Synthesis", 2ⁿᵈ ed., 1991, pp 10–12.

*Primary Examiner*—Ba K. Trinh
*Attorney, Agent, or Firm*—Finnegan, Henderson, Farabow, Garrett & Dunner, L.L.P.

[57] ABSTRACT

This invention relates to a taxoid of the formula (I):

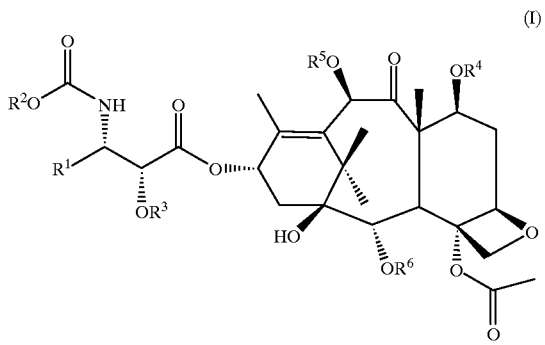

wherein
  $R^1$ is a $C_3$–$C_5$ alkyl or alkenyl or trifluoromethyl radical;
  $R^2$ is a $C_3$–$C_5$ branched alkyl radical;
  $R^3$ and $R^4$ are independently selected from hydrogen and hydroxyl protecting groups including functional groups which increase the water solubility of the taxoid antitumor agent;
  $R^5$ is a hydrogen, an acyl radical, or an alkoxylcarbonyl or carbamoyl radical; and
  $R^6$ is an acyl radical.

The compounds of formula I are useful as antitumor agents or their precursors. This invention also relates to a pharmaceutical composition having antineoplastic activity comprising the compound of formula (I) and a physiologically acceptable carrier and method of treatment using the compound of formula I.

16 Claims, No Drawings

TAXOID ANTI-TUMOR AGENTS AND PHARMACEUTICAL COMPOSITIONS THEREOF this application is a continuation-in-part of Ser. No. 08/330,956, filed Oct. 28, 1994, now abandoned.

FIELD OF INVENTION

The present invention relates to new taxoids possessing strong antitumor activities, the precursors of these antitumor taxoids, and pharmaceutical compositions thereof.

BACKGROUND OF THE INVENTION

Taxol (paclitaxel), a complex diterpene, is currently considered the most exciting lead in cancer chemotherapy. Paclitaxel possesses high cytotoxicity and strong antitumor activity against different cancers which have not been effectively treated by existing antitumor drugs. For example, paclitaxel has been approved by FDA in late 1992 for the treatment of advanced ovarian cancer and for breast cancer in 1994. Paclitaxel is currently in phase II and III clinical trial for lung cancer and other cancers.

Although paclitaxel is an extremely important "lead" in cancer chemotherapy, it is common that better drugs can be derived from naturally occurring lead compounds. In fact, French researchers have discovered that a modification of the C-13 side chain of paclitaxel brought about a new anticancer agent which seems to have antitumor activity superior to paclitaxel with better bioavailability. This unnatural compound was named "Taxotère (docetaxel)", which has t-butoxycarbonyl instead of benzoyl on the amino group of (2R,3S)-phenylisoserine moiety at the C-13 position and a hydroxyl group instead of acetoxy group at C-10. Docetaxel is currently in phase II and III clinical trials in United States, Europe, and Japan, has shown excellent activity, especially against breast and lung cancers.

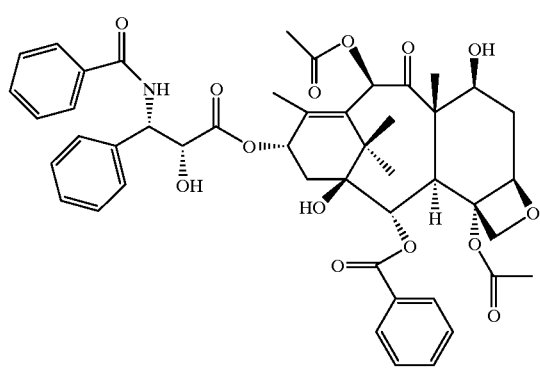

Taxol (paclitaxel)

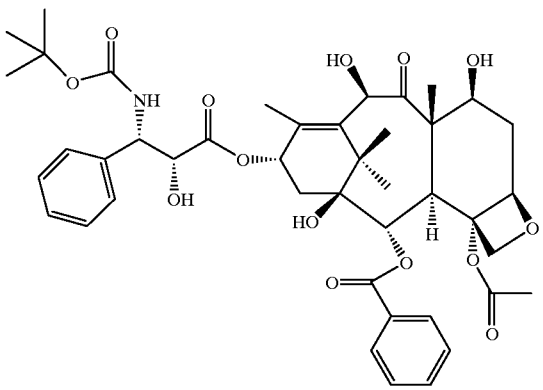

Taxotere (docetaxel)

A recent report on clinical trials of paclitaxel and docetaxel has disclosed that paclitaxel causes, e.g., nerve damage, muscle pain or disturbances in heart rhythm, whereas docetaxel provokes, e.g., mouth sores and a plunge in white blood cells. Other less serious side effects also exist for these two drugs. Therefore, it is very important to develop new anti-cancer drugs different from these two drugs which have fewer undesirable side effects, better pharmacological properties, improved activity against drug-resistant tumors, and/or activity spectra against various tumor types.

It is an objective of the present invention to develop such new anti-tumor agents of paclitaxel class, i.e., taxoids, which have distinct structural differences from those of paclitaxel and docetaxel.

It is an object of the present invention to provide a series of new taxoids bearing a 1-propenyl, 2-methyl-1-propenyl, 2-methylpropyl, or trifluromethyl radical at the C-3' position instead of a phenyl group, and which possess strong antitumor activities with better therapeutic profile, in particular against drug-resistant tumors. One of the serious drawbacks of both paclitaxel and docetaxel is the fact that these two drugs possess only a weak activity against drug-resistant tumors, e.g., adriamycin-resistant breast cancer. The new taxoids of the present invention have shown not only stronger antitumor activities against human ovarian, non-small cell lung, colon, and breast cancers than those of the two drugs, but also exhibit more than one order of magnitude better activity against adriamycin-resistant human breast cancer cells than those of the two drugs. Multi-drug-resistance (MDR) is a serious issue in clinical oncology, and thus the new taxoid antitumor agents of this invention will serve as important drugs to overcome this problem.

SUMMARY OF THE INVENTION

A taxoid of the formula (I)

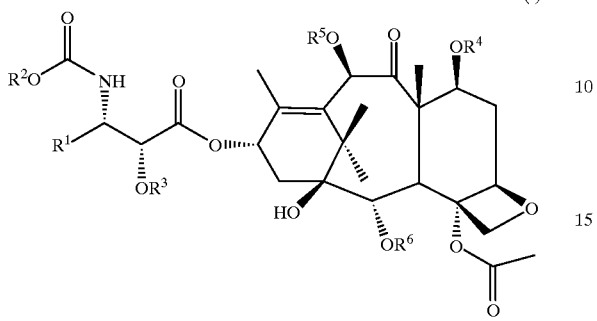

in which $R^1$ is a $C_3$–$C_5$ alkyl or alkenyl or trifluoromethyl radical;

$R^2$ is a $C_3$–$C_5$ branched alkyl radical;

$R^3$ and $R^4$ are independently selected from hydrogen and hydroxyl protecting groups including functional groups which increase the water solubility of the taxoid antitumor agent;

$R^5$ represents a hydrogen or hydroxyl-protecting an acyl or alkoxycarbonyl or carbamoyl group;

$R^6$ represents an acyl radical, which are useful as antitumor agents or their precursors.

Preferably, $R^1$ is selected from propyl, 2-methyl-1-propenyl, 1-methyl-1-propenyl, 2-methylpropyl, 1-methylpropyl, tert-butyl, cyclopropyl, cyclopropylmethyl, 1-methyl-1-butenyl, 2-methyl-1-butenyl, 3-methyl-1-butenyl, 1-methylbutyl, 2-methylbutyl, isobutyl, 2-methylethyl, 3-methylbutyl, 2-butenyl, or trifluoromethyl radicals;

$R^2$ is selected from isopropyl, cyclopropyl, isobutyl, sec-butyl, 2-methylpropyl, 3-methylpropyl, tert-butyl, cyclobutyl, cyclopentyl, 1-ethylpropyl, or 1,1-dimethylpropyl radicals;

$R^5$ is selected from hydrogen, $C_2$–$C_6$ acyl, $C_1$–$C_6$ alkoxylcarbonyl, $C_1$–$C_6$ N-alkylcarbamoyl, or $C_1$–$C_6$ N,N-dialkylcarbamoyl radicals; and $R^6$ is selected from benzoyl, fluorobenzoyl, chlorobenzoyl, azidobenzoyl, cyclohexanecarbonyl, acryloyl, crotonoyl, 1-methylacryloyl, 2-methyl-2-butenoyl, or 3-methyl-3-butenoyl radical.

More preferably, $R^5$ is selected from acetyl, propanoyl, cyclopropanecarbonyl, acryloyl, crotonoyl, 3,3-dimethylacryloyl, N-methylcarbamoyl, N-ethylcarbamoyl, N,N-dimethylcarbamoyl, N,N-diethylcarbamoyl, pyrrolidine-N-carbonyl, piperidine-N-carbonyl, morpholine-N-carbonyl, methoxycarbonyl, ethoxylcarbonyl, propoxylcarbonyl, butoxycarbonyl, cyclopentanecarbonyl, or cyclohexanecarbonyl radicals.

These new taxoids (I) are synthesized by the processes which comprise the coupling reactions of the baccatin of the formula (II)

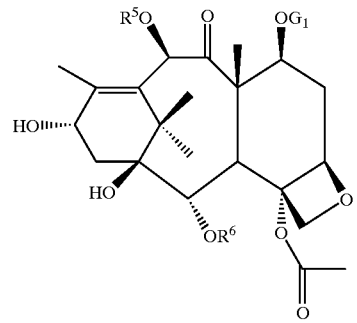

wherein $G_1$ represents a hydroxyl protecting group, and $R^5$ and $R^6$ have been defined above, with the β-lactams of the formula (III)

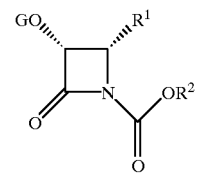

wherein G is a hydroxyl protecting group such as ethoxyethyl (EE), triethylsilyl (TES), (tert-butyl)dimethylsilyl (TBS), and triisopropylsilyl (TIPS), and $R^1$ and $R^2$ have been defined above, in the presence of a base.

DETAILED DESCRIPTION OF THE INVENTION

New taxoids of the formula (I) hereinabove are useful as antitumor agents or their precursors. These taxoids possess strong antitumor activities against human breast, non-small cell lung, ovarian, and colon cancers including drug-resistant cancer cells, as well as leukemia and melanoma.

The new taxoids of the formula (I) are synthesized by modifying the baccatins of the formula (II)

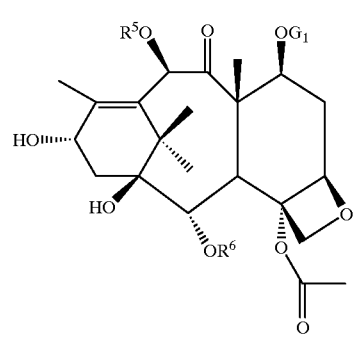

wherein $G_1$, $R^5$, and $R^6$ have been defined above.

The baccatins (II) are coupled with the β-lactams of the formula (III)

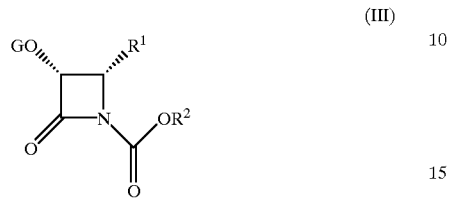

wherein G, $R^1$, and $R^2$ have been defined hereinabove, to yield the new taxoids (I)

The β-lactams (III) are readily prepared via the β-lactams (IV) which are easily obtained through the chiral enolate-imine cyclocondensation method that has been developed in the present inventor's laboratory as shown in Scheme 1 (Ojima et al., Bioorg. Med. Chem. Lett., 1993, 3, 2479, Ojima et al., Tetrahedron Lett., 1993, 34, 4149, Ojima et al., Tetrahedron Lett. 1992, 33, 5739, Ojima et al., Tetrahedron, 1992, 48, 6985, Ojima, I. et al., J. Org. Chem., 1991, 56, 1681, the disclosures of which are incorporated herein by reference). In this preparation, the β-lactams (IV) with extremely high enantiomeric purities are obtained in high yields. In Scheme 1, R* is a chiral auxiliary moiety which is (-)-trans-2-phenyl-1-cyclohexyl or (-)-10-dicyclohexylsulfamoyl-D-isobornyl, TMS is a trimethylsilyl radical, and the base is lithium diisopropylamide or lithium hexamethyldisilazide and G and $R^1$ have been defined hereinabove.

The β-lactams (IV) can be converted to the corresponding N-alkoxycarbonyl-β-lactams (III) in excellent yields by reacting with alkyl chloroformates in the presence of a base (Scheme 2). This transformation is known to those skilled in the art.

The β-lactams (III) are readily used for the coupling with the baccatins (II) in the presence of a base, followed by deprotection to give the new taxoids (I) in high yields (Scheme 3).

Scheme 2:

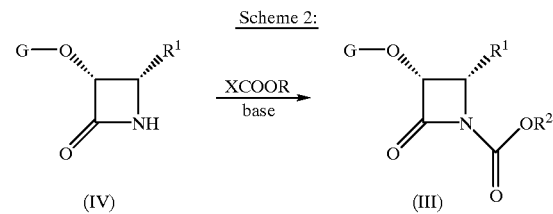

Scheme 1:

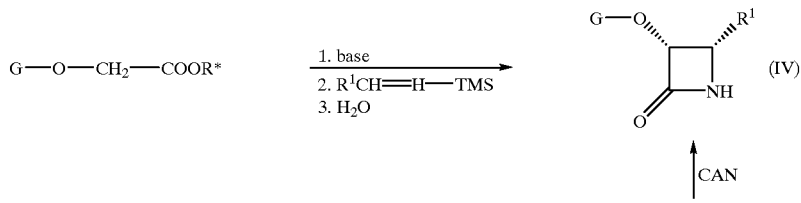

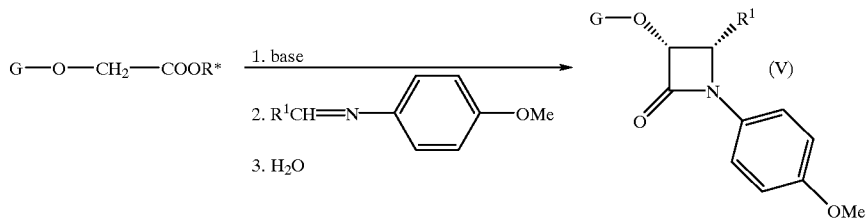

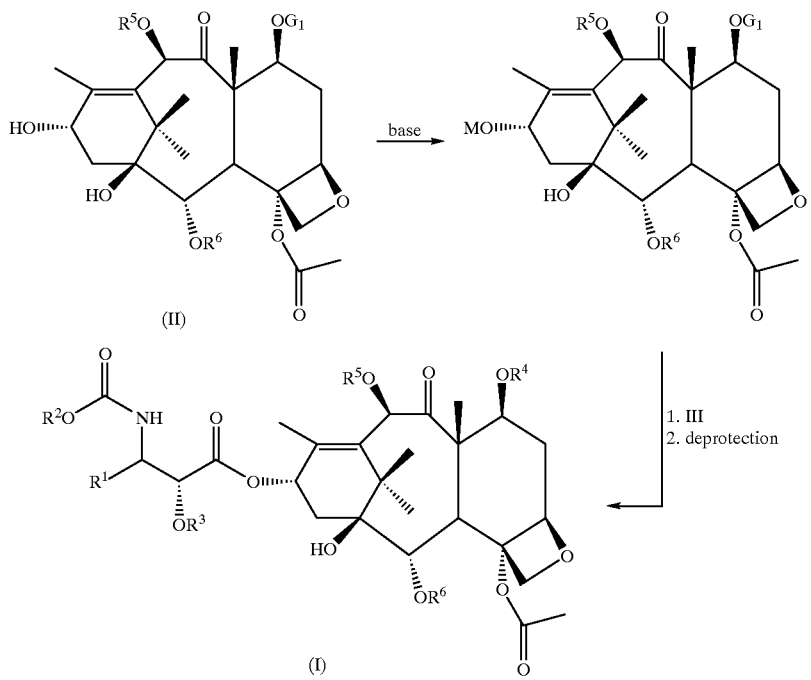

Scheme 3:

In Schemes 1–3, $R^1$ through $R^6$ have been defined above, M is an alkali metal, and the hydroxyl protecting group $G_1$ is independently selected from methoxylmethyl (MOM), methoxyethyl (MEM), 1-ethoxyethyl (EE), benzyloxymethyl, (β-trimethylsilylethoxyl)-methyl, tetrahydropyranyl, 2,2,2-trichloroethoxylcarbonyl (Troc), benzyloxycarbonyl (CBZ), tert-butoxycarbonyl (t-BOC), 9-fluorenylmethoxycarbonyl (Fmoc), 2,2,2-trichloroethoxymethyl trimethylsilyl, triethylsilyl, tripropylsilyl, dimethylethylsilyl, dimethyl(t-butyl)silyl, diethylmethylsilyl, dimethylphenylsilyl, diphenylmethylsilyl, acetyl, chloroacetyl, dichloroacetyl, trichloroacetyl and trifluoroacetyl.

The coupling reaction of the baccatin (II) and the β-lactams (VI) is carried out via an alkali metal alkoxide of the baccatin (II) at the C-13 hydroxyl group. The alkoxide can readily be generated by reacting the baccatin with an alkali metal base such as sodium hexamethyldisilazide, potassium hexamethyldisilazide, lithium hexamethyldisilazide, sodium diisopropylamide, potassium diisopropylamide, lithium diisopropylamide, sodium hydride, in a dry nonprotic organic solvent such as tetrahydrofuran (THF), dioxane, ether, dimethoxyethane (DME), diglyme, dimethylformamide (DMF), mixtures of these solvents with hexane, toluene, and xylene, in a preferred temperature range from about –100° C. to about 50° C., more preferably at about –78° C. to about 25° C. This reaction is preferably carried out under inert atmosphere such as nitrogen and argon. The amount of the base used for the reaction is preferably approximately equivalent to the amount of the baccatin when soluble bases such as sodium hexamethyldisilazide, potassium hexamethyldisilazide, lithium hexamethyldisilazide, sodium diisopropylamide, potassium diisopropylamide, lithium diisopropylamide are used. The use of a slight excess of the base does not adversely affect the reaction. When heterogeneous bases such as sodium hydride and potassium hydride are used, 5–10 equivalents of the base (to the amount of the baccatin) are preferably employed.

The coupling reaction of the metal alkoxide of the baccatin thus generated with the β-lactam is typically carried out by adding the solution of the β-lactam in a dry organic solvent exemplified above in a preferred temperature range from about –100° C. to 50° C., more preferably at about –35° C. to 25° C. The mixture of reactants is stirred for 15 minutes to 24 hours and the progress and the completion of the reaction is monitored by thin layer chromatography (TLC), for example. When the limiting reactant is completely consumed, the reaction is quenched by addition of a cold brine solution. The crude reaction mixture is worked up using the standard isolation procedures which are generally known to those skilled in the art to give the corresponding taxoid. The proportion of the β-lactam and the baccatin is in a range from 2:1 to 1:2, more preferably approximately 1:1 for purposes of economy and efficiency, but the ratio is not critical for the reaction.

The hydroxyl protecting groups can then be removed by using the standard procedures which are generally known to those skilled in the art to give the desired taxoid derivatives. For example, EE and TES groups can be removed with 0.5 N HCl at room temperature for 36 h, TIPS and TBS groups can be removed by treating with fluoride ion or HF in a non-protic organic solvent, and Troc group can be removed with zinc and acetic acid in methanol at 60° C. for 1 hour without disturbing the other functional groups and the skeleton of the taxoid.

It has been shown that the introduction of 2-methyl-1-propenyl group to the C-3' position of paclitaxel appears to increase the cytotoxicity, especially against drug-resistant cancer cells: Holton and Nadizadeh disclosed in U.S. Pat. No. 5,284,864 (1994) that 3'-desphenyl-3'-isobutenylpaclitaxel (RAH-1) exhibited 4 times better activity than paclitaxel and 7 times better activity than docetaxel against human colon carcinoma cells HCT-116, and also about 20 times better activity than paclitaxel and 9 times better activity than docetaxel against multi-drug resistant phenotype human colon carcinoma cells HCT-116/VM.

We have found that the structural requirements for taxoid antitumor agents to express strong potency are rather strict and unpredictable. For example, 3'-desphenyl-3'-(2-phenylethenyl)docetaxel, bearing 2-phenylethenyl group instead of the isobutenyl group of RAH-1, has dramatically decreased cytotoxicity (>20 times) and 3'-desphenyl-3'-neopentyldocetaxel, bearing neopentyl group which has just one more methyl than isobutenyl group, is virtually not cytotoxic against A121 human ovarian, A549 human non-small cell lung, HT-29 human colon and MCF7 human breast cancer cells. While looking at the structure-activity relationships (SAR) of new taxoids that have different substituents at the C-3' and C-10, we discovered that there are optimum combinations of these two substituents which achieve extraordinarily high activity against drug-resistant cancer cells.

After searching for the best substituent for the C-3' and the C-10 positions by employing many alkyl groups and alkenyl groups by trial and error, we have identified 1-propenyl, 2-methyl-1-propenyl, 2-methylpropyl, and trifluoromethyl groups to be the optimum substituents for the C-3' position, and acyl groups, alkoxycarbonyl groups, and N,N-dialkylcarbamoyl groups to be the optimum substituents for the C-10 position.

For example, 3'-desphenyl-3'-(1-propenyl)-10-acetyldocetaxel (Taxoid Ia) showed a substantially better activity spectrum than that of paclitaxel and docetaxel against human ovaian, human non-small cell lung, human colon, and human breast cancer cells mentioned above (see TABLE 1 in EXAMPLE 32). Moreover, this agent possesses 21 times better activity than paclitaxel and 17 times better activity than docetaxel against the drug-resistant human breast cells MCF7-R, which are mammary carcinoma cells 180 fold resistant to a widely used anticancer drug, adriamycin. In the same assay, Holton's compound RAH-1 showed only marginal activity that was one order of magnitude weaker than that of Taxoid Ia (see TABLE 1 in EXAMPLE 32).

3'-Desphenyl-3'-(2-methyl-1-propenyl)-10-cyclopropanecarbonyldocetaxel (Taxoid IX) showed one order of magnitude better activity than that of paclitaxel and docetaxel against human human breast cancer cells mentioned above (see TABLE 2 in Example 32), and possesses two order of magnitude (142 times) better activity against the drug-resistant human breast cells mentioned above. These extraordinarily high activities are totally unpredictable from the exsisting SAR studies of paclitaxel and docetaxel, and thus demonstrate the exceptional importance of our discovery.

The taxoids of the formula (I) of this invention are useful for inhibiting tumor growth or regression of tumors in animals including humans and are preferably administered in the form of a pharmaceutical composition including effective amounts of the antitumor agent of this invention in combination with a pharmaceutically acceptable vehicle or diluent.

The pharmaceutical compositions of the antitumor agents of the present invention may be made in any form suitable for desired use, e.g., oral, parenteral or topical administration. Examples of parenteral administration are intramuscular, intraveneous, intraperitoneal, rectal, and subcutaneous administration. The vehicle or diluent ingredients should not reduce the therapeutic effects of the antitumor agents of this invention.

Suitable dosage forms for oral use include tablets, dispersible powders, granules, capsules, suspension, syrups, and elixirs. Examples of inert diluents and vehicles for tablets include calcium carbonate, sodium carbonate, lactose and talc. Examples of inert diluents and vehicles for capsules include calcium carbonate, calcium phosphate, and kaolin. Dosage forms appropriate for parenteral administration include solutions, suspensions, dispersions, and emulsions.

The water solubility of the antitumor agents of the formula (I) may be improved by modifying the C-2' and /or C-7 substituents to incorporate suitable functional groups, such as $R^3$ and $R^4$. In order to increase the water solubility, $R^3$ and $R^4$ can be independently selected from hydrogen and —CO—X—Y, wherein X is selected from —$(CH_2)_n$— (n=1–3), —CH=CH—, cyclohexanediyl, and benzenediyl and Y is selected from —COOH and its pharmaceutically acceptable salts, —$SO_3H$ and its pharmaceutically acceptable salts, —$NR^7R^8$ and its pharmaceutically acceptable salts, the pharmaceutically acceptable ammonium salt —$NR^7R^8R^9$, —$CONR^8R^9$, or —$COOR^9$, in which —$NR^7R^8$ includes cyclic amine radicals selected from pyrrolidinyl, piperidinyl, morphorino, piperazinyl, and N-methylpiperazinyl;

$R^7$ and $R^8$ are independently selected from hydrogen, allyl, $C_1$–$C_6$ alkyl, and —$(CH_2)_n$—Z (n=1–3);

$R^9$ is selected from $C_1$–$C_6$ alkyl, allyl, and —$(CH_2)_n$—Z (n=1–3), and

Z is selected from —COOH and its pharmaceutically acceptable salts, —$SO_3H$ and its pharmaceutically acceptable salts, —$NR^7R^8$ and its pharmaceutically acceptable salts, and pharmaceutically acceptable ammonium salt —$NR^7R^8R^{10}$, in which $R^{10}$ is selected from hydrogen, allyl, and $C_1$–$C_6$ alkyl.

The preparation of the water-soluble analogs of paclitaxel bearing the functionalized acyl groups described above has been disclosed in Kingston et al., U.S. Pat. No. 5,059,699 (1991); Stella et al., U.S. Pat. No. 4,960,790 (1990), the disclosures of which are incorporated herein by reference, and thus it is not difficult for the people in the art to carry out such modifications.

The following non-limiting examples are illustrative of the present invention. It should be noted that various changes could be made in the examples and processes therein without departing from the scope of the present invention. For this reason, it is intended that the illustrative embodiments of the present application should be interpreted as being illustrative and not limiting in any sense.

EXAMPLE 1

(−)-(1R,2S)-2-phenyl-1-cyclohexyl triisopropylsilyloxyacetate:

A solution of (−)-(1R,2S)-2-phenyl-1-cyclohexyl hydroxyacetate (851 mg, 3.63 mmol) was prepared through esterification of benzyloxyacetyl chloride with (−)-(1R,2S)-2-phenyl-1-cyclohexanol followed by hydrogenolysis. Then, triisopropylsilyl chloride (840 mg, 4.36 mmol) and imidazole (618 mg, 9.08 mmol) in dimethylformamide (DMF) (1.7 mL) was added and stirred at room temperature for 12–20 hours. The mixture was poured into pentane (25 mL), and washed with water and brine. The combined organic layers were dried over anhydrous $MgSO_4$ and concentrated in vacuo. The crude product was subjected to a purification on a short silica gel column using hexane/chloroform (3/1) as the eluant to give pure (−)-(1R,2S)-2-phenyl-1-cyclohexyl triisopropylsilyloxyacetate (1.35 g, 95% yield) as a colorless oil: $[\alpha]_D^{20}$ −17.1° (c 3.15, $CHCl_3$), IR (neat) 1759, 1730 ("CO) $cm^{-1}$; $^1H$ NMR ($CDCl_3$) δ0.93–0.99 (m, 21H), 1.30–1.62 (m, 4H), 1.72–2.0 (m, 3H), 2.10–2.19 (m, 1H), 266 (dt, J=11.5, 4.0 Hz, 1H), 3.90 (d, J=16.6 Hz, 1H), 4.07 (d, J=16.6 Hz, 1H), 5.07 (dt, J=10.6, 4.0 Hz, 1H), 7.16–7.30 (m, 5H). Anal. Calcd for $C_{23}H_{38}O_3Si$: C, 70.72; H, 9.81 Found: C, 70.79; H, 9.85.

EXAMPLES 2–3

N-(4-Methoxyphenyl)-2-alkenylaldimine:

To a solution of 0.360 g. (2.9 mmol) of p-anisidine (recrystallized twice from ethanol) in 12 mL of $CH_2Cl_2$ over anhydrous $Na_2SO_4$ was added 0.24 g (3.5 mmol) of 2-butenal (crotonaldehyde) (distilled immediately prior to use) under nitrogen. After 4 hours, $Na_2SO_4$ was filtered off and the solvent removed under vacuum to give N-(4-methoxyphenyl)-2-butenaldimine in quantitative yield, which was used for the synthesis of β-lactam without further purification.

In the same manner, N-(4-methoxyphenyl)-3-methyl-22-butenaldimine was obtained in quantitative yield.

EXAMPLES 4–5
(3R,4S)-1-(4-Methoxyphenyl)-3-triisopropylsilyloxy-4-(1-alkenyl)azetidin-2-one (V):

To a solution of 0.27 mL (1.9 mmol) of diisopropylamine in 10 mL of THF was added 0.76 mL (1.9 mmol) of 2.5M n-butyllithium in hexanes at −10° C. After stirring for 45 minutes, the solution was cooled to −85° C. A solution of (−)-(1R,2S)-2-phenyl-1-cyclohexyl triisopropylsilyloxy-acetate (0.575 g 1.47 mmol) in 10 mL of THF was added via cannula over a period of 1.5 hours. After stirring for an additional hour, a solution of N-(4-methoxyphenyl)-2-butenaldimine (336 mg, 2.2 mmol) in 10 mL of THF was added via cannula over a period of approximately 1 hour. The mixture was stirred for 2 hours and allowed to warm up to room temperature overnight while stirring. The reaction was then quenched with saturated NH$_4$Cl. The aqueous layer was extracted with ethyl acetate (EtOAc) and the combined organic layers were washed with saturated NH$_4$Cl solution, and brine, and then dried over MgSO$_4$. After the removal of solvent under vacuum, the crude product was obtained, which was purified by flash chromatography on silica gel (hexane:EtOAc=10:1 to 6:1) to afford pure PMP-β-lactam Va (399 mg, 70% yield) as a rust-colored oil. The enantiomeric purity of the PMP-β-lactam Va was determined to 97% ee on the basis of chiral HPLC analysis: $[\alpha]_D$=+33.1° (c 0.27, CHCl$_3$); $^1$H NMR (CDCl$_3$, 250 MHz) δ1.04–1.16 (m, 21H), 1.76 (dd, J=6.5, 1.3 Hz, 3H), 3.74 (s, 3H), 4.51 (dd, J=8.6, 5.0 Hz, 1H), 5.04 (d, J=5.0 Hz, 1H), 5.59 (ddd, J=15.4, 8.6, 1.3 Hz, 1H), 5.92 (dq, J=15.4, 6.5 Hz, 1H), 6.83 (d, J=9.0, 2H), 7.36 (d, J=9.0 Hz, 2H); $^{13}$C NMR (63 MHz, CDCl$_3$) d 11.89, 17.63, 17.68, 55.38, 61.89, 77.57, 114.18, 118.48, 126.65, 127.48, 128.34, 128.55, 132.59, 156.03. 165.43.

In the same manner, PMP-β-lactam Vb (R$^1$=2-methyl-1-propenyl) was obtained in 73% yield (93% ee): $[\alpha]_D$=+65.7° (c 1.00, CHCl$_3$); $^1$H NMR (CDCl$_3$, 300 MHz) δ1.08–1.12 (m, 21 H), 1.81 (s, 3 H), 1.86 (s, 3 H), 3.78 (s, 3 H), 4.79–4.84 (dd, J=5.1, 9.9 Hz, 1 H), 5.05–5.07 (d, J=5.1 Hz, 1 H), 5.33–5.36 (bd, J=9.9 Hz, 1 H); $^{13}$C NMR (CDCl$_3$, 63 MHz) d 11.92, 17.61, 18.33, 26.11, 55.44, 57.56, 76.51, 77.015, 77.52, 114.25, 118.34, 120.15, 128.73, 131.52, 139.14, 156.00, 165.61.

EXAMPLES 6–7
(3R,4S)-3-Triisopropylsilyloxy-4-(1-alkenyl)azetidin-2-one (IV):

To a solution of 260 mg. (0.67 mmol) of N-PMP-β-lactam Va in 20 ml. of acetonitrile at −10° C., was added dropwise a solution of 1.13 g (2.07 mmol) of cerium ammonium nitrate (CAN) in 25 mL of water. The mixture was allowed to stir for 1 hour and then diluted with 50 mL of water. The aqueous layer was extracted with ethyl acetate (2×35 mL) and the combined organic layers were washed with water, 5% NaHSO$_3$, 5% Na$_2$CO$_3$, and brine. After drying over MgSO$_4$ and concentrating under vacuum, the organic layers afforded the crude product, which was purified on a silica gel column using hexane-ethyl acetate as the eluant (hexane:EtOAc=3:1) to give the pure β-lactam IVa (R$^1$=1-propenyl) (124 mg, 65% yield) as a pale yellow viscous oil: $^1$H NMR (CDCl$_3$, 250 MHz) δ1.04–1.16 (m, 21H), 1.70 (dd, J=6.5, 1.2 Hz, 3H), 4.13 (dd, J=8.7, 4.9, 1H), 4.94 (d, J=4.9 Hz, 1H), 5.51 (ddd, J=14.1, 8.7, 1.2 Hz, 1H), 5.67 (m, 1H), 6.68 (br s, 1H); $^{13}$C NMR (63 MHz, CDCl$_3$) d 11.80, 17.57, 17.62, 58.14, 79.18, 127.97, 130.64, 170.36.

In the same manner, β-lactam IVb (R$^1$=2-methyl-1-propenyl) was obtained in 94% yield: $^1$H NMR (CDCl$_3$, 300 MHz) δ1.02–1.10 (m, 21 H), 1.65 (s, 3 H), 1.72 (s, 3 H), 4.36–4.40 (dd, J=4.5, 9.6 Hz, 1 H), 4.91–4.93 (dd, J=2.1, 4.5 Hz, 1H), 5.23–5.26 (bd, J=9.6 Hz, 1 H), 6.28 (bs, 1 H, NH).

EXAMPLES 8–9
(3R,4S)-1-tert-Butoxycarbonyl-3-triisopropylsilyloxy-4-(1-alkenyl)azetidin-2-one (III):

To a solution of 100 mg (0.35 mmol) of the β-lactam IVa, 0.24 mL (1.75 mmol) of triethylamine, and a catalytic amount of dimethylaminopyridine (DMAP) in 11 mL of CH$_2$Cl$_2$, was added dropwise at room temperature, 85 mg. (0.38 mmol) of di(tert-butyl) dicarbonate in 2 mL of CH$_2$Cl$_2$. The mixture was stirred for 1 hour and quenched with saturated NH$_4$Cl solution. The mixture was diluted with 60 mL of ethyl acetate and the organic layer was washed with brine, dried over MgSO$_4$, and concentrated. The crude product was purified by flash chromatography on silica gel (hexane:EtOAc=4:1) to yield pure N-$^t$BOC-β-lactam IIIa (R$^1$=1-propenyl) as colorless oil (105 mg, 87% yield): $^1$H NMR (CDCl$_3$, 250 MHz) δ1.02–1.08 (m, 21H), 1.48 (s, 9H), 1.74 (dd, J=6.4, 1.3 Hz, 3H), 4.44 (dd, J=8.6, 5.8 Hz, 1H), 4.94 (d, J=5.8 Hz, 1H), 5.54 (ddd, J=15.4, 8.6, 1.3 Hz), 5.83 (dq, J=15.4, 6.4 Hz, 1H); $^{13}$C NMR (63 MHz, CDCl$_3$) δ11.76, 17.52, 17.95, 27.97, 61.04, 83.06, 124.80, 132.72, 148.0, 166.07. Anal. Calcd for C$_{20}$H$_{37}$NO$_4$Si: C, 62.62, H, 9.72, N, 3.65. Found: C, 62.62; H, 9.63; N, 3.61.

In the same manner, N-$^t$BOC-β-lactam IIIb (R$^1$=2-methyl-1-propenyl) was obtained as a colorless oil in 82% yield: $^1$H NMR (CDCl$_3$, 300 MHz) δ0.97–1.06 (m, 21 H), 1.48 (s, 9 H), 1.75 (s, 3 H), 1.78 (s, 3 H), 4.72–4.77 (dd, J=5.7, 9.9 Hz, 1 H), 4.94–4.96 (dd, J=5.7 Hz, 1 H), 5.25–5.28 (bd, J=9.9 Hz , 1 H).

EXAMPLES 10–15
7-Triethylsilyl-10-O-substituted 10-deacetylbaccatin III (IIb-g).

To a solution of 1.0 g (1.84 mmol) of 10-deacetylbaccatin III and 375 mg (5.52 mmol) of imidazole in 10 mL DMF was added dropwise 0.9 mL (5.52 mmol) of chlorotriethylsilane (TESCl). The reaction mixture was stirred for 5 hours at room temperature and quenched with water, then diluted with EtOAc. The aqueous layer was extracted with EtOAc and the combined organic layers were washed with water, dried over MgSO$_4$, and concentrated. The crude product was purified by flash chromatography on silica gel (hexane/EtOAc, 1:1) to give 774 mg (64%) of 7-triethylsilyl-10-deacetylbaccatin III (7-TES-DAB) as a white solid: $^1$H NMR (CDCl$_3$, 250 MHz) δ0.50 (m, 6 H), 0.97 (m, 9 H), 1.21 (s, 3 H), 1.58 (s, 3 H), 1.73 (s, 3 H), 1.85 (dt, 1 H), 1.99 (s, 3 H), 2.23 (s, 3 H), 2.24 (s, 2 H), 2.47 (ddd, 1 H), 3.94 (d, J=7.2 Hz, 1 H), 4.14 (AB, J$_{AB}$=8.4 Hz, 1 H), 4.32 (AB, J$_{AB}$=8.1 Hz, 1 H), 4.41 (d, J=6.3 Hz, 1 H), 4.84 (t, 1 H), 4.94 (d, J=8.4 Hz, 1 H), 5.14 (s, 1 H), 5.19 (s, 1 H), 5.58 (d, J=7.2 Hz, 1 H), 7.40 (t, 2 H), 7.54 (t, 1 H), 8.10 (d, 2 H).

To 77 mg (0.117 mmol) of 7-TES-DAB in 5 mL THF was added 0.12 mL of LiHMDS (1M in THF). The reaction mixture was stirred at −40° C. for 5 minutes, then 0.010 mL (0.117 mmol) of propanoyl chloride (previously distilled) was added. The solution was allowed to warm up at 0° C. over a 30 min period. Then the solvent was removed in vacuo and the crude product was purified by flash chromatography on silica gel (hexane then hexane/EtOAc, 4:1, then 2:1 and 1:1) to afford 60 mg (72%) of 7-triethylsilyl-10-propanoyl-10-deacetylbaccatin III (IIb) as a white solid: $[\alpha]_D^{21}$−68.57° (c 1.75, CHCl$_3$); $^1$H NMR (CDCl$_3$, 250 MHz) δ0.52 (q, 6 H), 0.87 (t, 9 H), 1.02 (s, 3 H), 1.16–1.22 (m 6 H), 1.55 (s, 9 H), 1.67 (s, 3 H), 1.86 (m, 1 H), 2.19 (s, 3 H), 2.25 (s, 2 H), 2.27 (s, 3 H), 2.42 (m, 3 H), 3.86 (d, J=6.9 Hz, 1 H), 4.12 (AB, J$_{AB}$=8.0 Hz, 1 H), 4.27 (AB, J$_{AB}$=8.0 Hz, 1 H), 4.49 (dd, 1 H), 4.83 (t, 1 H), 4.93 (d, J=9.2 Hz, 1 H), 5.61 (d, J=6.9 Hz, 1 H), 6.46 (s, 1 H), 7.43 (t, 2 H), 7.56 (t, 1 H), 8.08 (d, 2 H); $^{13}$C NMR (CDCl$_3$, 63 MHz) δ5.2, 6,7, 9.2, 9.9, 14.9, 20.1, 22.6, 26.7, 27.6, 37.2, 38.3, 42.7, 58.6, 67.8, 72.3, 74.7, 75.5, 76.5. 77.0, 77.5, 78.7, 80.8, 84.2, 128.5, 129.4, 130.0, 132.6, 133.5, 143.9, 167.8, 170.7, 174.5, 202.3. IR (neat, cm$^{-1}$) 2953, 2913, 1789, 1738, 1715, 1681, 1454, 1434, 1392, 1362, 1315, 1175, 1108. HRMS (FAB, DCM/NBA) m/z: Calcd. for $C_{38}H_{54}O_{11}SiH^+$, 715.3513. Found, 715.3552.

In the same manner, the following 7-triethylsilyl-1-O-substituted-10-deacetylbaccatin IIIs were prepared.

7-Triethylsilyl-10-cyclopropanecarbonyl-10-deacetylbaccatin III (IIc).

White solid; $[\alpha]_D^{21}$ −61.42° (c 7.00, CHCl$_3$); $^1$H NMR (CDCl$_3$, 250 MHz) δ0.46 (m, 6 H), 0.82 (m, 9 H), 0.97 (s, 3 H), 1.12 (s, 3 H), 1.18 (m, 2 H), 1.60 (s, 3 H), 1.68 (m, 2 H), 1.79 (m, 1 H), 2.12 (s, 3 H), 2.16 (s, 2 H), 2.20 (s, 3 H), 2.40 (m, 1 H), 2.50 (d, 1 H), 3.79 (d, J=6.9 Hz, 1 H), 4.03 (AB, $J_{AB}$=8.1 Hz, 1 H), 4.24 (AB, $J_{AB}$=8.1 Hz, 1 H), 4.38 (dd. J=6.6 Hz, 10.1 Hz, 1 H), 4.75 (t, 1 H), 4.87 (d, J=9.0 Hz, 1 H), 5.55 (d, J=6.6 Hz, 1 H), 6.39 (s, 1 H), 7.37 (t, 2 H), 7.51 (t, 1 H), 8.02 (d, 2 H); IR (neat, cm$^{-1}$) 2958, 2356, 1771, 1732, 1716, 1699, 1652, 1558, 1456, 1393, 1268, 1169, 1107, 1070, 1026, 738. Anal. Calcd. for $C_{39}H_{54}O_{11}Si$: C, 64.44; H, 7.49. Found: C, 64.52, H, 7.49.

7-Triethylsilyl-10-crotonoyl-10-deacetylbaccatin III (IId).

White solid; $[\alpha]_D^{22}$ −68.57° (c 7.00, CHCl$_3$); $^1$H NMR (CDCl$_3$, 250 MHz) δ0.51 (q, 6 H), 0.86 (t, 9 H), 1.00 (s, 3 H), 1.20 (s, 3 H), 1.66 (s, 3 H), 1.80 (m, 1 H), 1.88 (d, 3 H), 2.19 (s, 2 H), 2.20 (s, 3 H), 2.26 (s, 3 H), 2.51 (m, 3 H), 3.87 (d, J=6.8 Hz, 1 H), 4.80 (AB, $J_{AB}$=8.2 Hz, 1 H), 4.26 (AB, $J_{AB}$=8.2 Hz, 1 H), 4.45 (dd, J=6.7 Hz, 9.9 Hz, 1 H), 4.80 (t, 1 H), 4.92 (d, J=9.7 Hz, 1 H), 5.61 (d, J=6.8 Hz, 1 H), 5.92 (d, J=15 Hz, 1 H), 6.48 (s, 1 H), 7.02 (m, 1 H), 7.42 (t, 2 H), 7.55 (t, 1 H), 8.07 (d, 2 H); $^{13}$C (CDCl$_3$, 63 MHz) δ5.2, 6.7, 9.9, 14.9, 18.1, 20.1, 22.6, 26.7, 37.2, 38.2, 42.7, 47.3, 58.6, 67.9, 72.3, 74.7, 75.5, 76.5, 77.0, 77.5, 78.7, 80.8, 84.2, 122.3, 128.5, 129.4, 130.0, 132.7, 133.6, 143.9, 145.6, 164.7, 167.1, 170.7, 202.3; IR (neat, cm$^{-1}$) 2953, 2356, 1716, 1558, 1455, 1267, 1173, 1106, 1001, 822.

7-Triethylsilyl-10-N,N-dimethylcarbamoyl-10-deacetylbaccatin III (IIe).

White solid; $[\alpha]_D^{21}$ −30° (c 2.00, CHCl$_3$); $^1$H NMR (CDCl$_3$, 300 MHz) δ0.57 (m, 6 H), 0.91 (m, 9 H), 1.21 (s, 3 H), 1.27 (s, 3 H), 1.69 (s, 3 H), 1.84 (dt, 1 H), 2.21 (s, 2 H), 2.26 (s, 3 H), 2.29 (s, 2 H), 2.49 (m, 1 H), 2.95 (s, 3 H), 3.09 (s, 3 H), 3.91 (d, J=6.9 Hz, 1 H), 4.12 (AB, $J_{AB}$=8.4 Hz, 1 H), 4.30 (AB, $J_{AB}$=8.4 Hz, 1 H), 4.48 (dd, J=6.7 Hz, 10.2 Hz, 1 H), 4.84 (t, 1 H), 4.97 (d, J=9.0 Hz, 1 H), 5.64 (d, J=6.9 Hz, 1 H), 6.40 (s, 1 H), 7.46 (t, 2 H), 7.59 (t, 1 H), 8.11 (d, 2 H). HRMS (FAB, DCM/NBA/NaCl) m/z: Calcd. for $C_{38}H_{55}O_{11}NSiNa^+$, 752.3442. Found, 752.3483.

7-Triethylsilyl-10-methoxycarbonyl-10-deacetylbaccatin III (IIf).

White solid; $[\alpha]_D^{22}$ −72.50° (c 4.00, CHCl$_3$); $^1$H NMR (CDCl$_3$, 300 MHz) δ0.54 (m, 6 H), 0.89 (m, 9 H), 1.03 (s, 3 H), 1.15 (s, 3 H), 1.67 (s, 3 H), 1.82 (dt, 1 H), 2.18 (s, 3 H), 2.25 (s, 2 H), 2.27 (s, 3 H), 2.47 (ddd, 1 H), 3.82 (s, 3 H), 3.84 (d, 1 H), 4.11 (AB, $J_{AB}$=8.1 Hz, 1 H), 4.27 (AB, $J_{AB}$=8.1 Hz, 1 H), 4.44 (dd, J=6.6 Hz, 10.2 Hz, 1 H), 4.83 (t, 1 H), 4.93 (d, J=9.0 Hz, 1 H), 5.59 (d, J=6.9 Hz, 1 H), 6.27 (s, 1 H), 7.43 (t, 2 H), 7.56 (t, 1 H), 8.07 (d, 2 H). IR (neat, cm$^{-1}$) 3524, 2957, 1715, 1442, 1371, 1266, 1108, 1025, 912, 820, 732.

7-Triethylsilyl-10-acryloyl-10-deacetylbaccatin III (IIg).

White solid; $[\alpha]_D^{22}$ −77.5° (c 4.00, CHCl$_3$); $^1$H NMR (CDCl$_3$, 250 MHz) δ0.51 (q, 6 H), 0.87 (t, 9 H), 1.01 (s, 3 H), 1.21 (s, 3 H), 1.68 (s, 3 H), 1.81 (m, 1 H), 2.15 (d, 2 H), 2.22 (s, 3 H), 2.27 (s, 3 H), 2.46 (m, 1 H), 3.87 (d, J=6.9 Hz, 1 H), 4.12 (AB, $J_{AB}$=8.3 Hz, 1 H), 4.28 (AB, $J_{AB}$=8.3 Hz, 1 H), 4.47 (dd, J=6.7 Hz, 10.2 Hz, 1 H), 4.81 (t, 1 H), 4.94 (d, J=8.7 Hz, 1 H), 5.62 (d, J=6.9 Hz, 1 H), 5.88 (d, J=10.7 Hz, 1 H), 6.18 (m, 1 H), 6.47 (m, 1 H), 6.51 (s, 1 H), 7.02 (m, 1 H), 7.43 (t, 2 H), 7.56 (t, 1 H), 8.08 (d, 2 H); $^{13}$C NMR (CDCl$_3$, 63 MHz) δ5.2, 6,7, 9.9, 14.9, 20.1, 22.6, 26.7, 37.2, 38.2, 42.7, 47.3, 58.6, 67.9, 72.3, 74.7, 75.8, 76.5, 77.0, 77.5, 78.7, 80.8, 84.2, 128.1, 128.5, 129.3, 130.0, 131.5, 132.5, 133.6, 144.2, 164.5, 167.0, 170.7, 202.0; IR (neat, cm$^{-1}$) 2950, 2250, 1734, 1717, 1653, 1635, 1506, 1457, 1362, 1269.

EXAMPLES 16–21

7-Triethylsilyl-10-O-substituted 2'-triisopropylsilyl-3'-(1-propenyl)docetaxel (I-P):

To a solution of 68 mg (0.097 mmol) of 7-triethylsilylbaccatin III (IIa) and 58 mg (0.15 mmol) of the N-$^t$BOC-β-lactam (VIa) in 4 mL of THF at −30° C. was added 0.12 mL (0.12 mmol) of LiHMDS. The mixture was allowed to warm to −10° C. and stirred for 1 hour and was then quenched with NH$_4$Cl. The aqueous layer was extracted with 75 mL of EtOAc and the combined organics were washed with NH$_4$Cl and brine. The organics were then dried over MgSO$_4$ and concentrated under vacuum. Upon purification by flash column chromatography on silica gel (hexane:EtOAc=4:1), 83 mg (79% yield) of pure protected taxoid 7-Triethylsilyl-10-acetyl-2'-triisopropylsilyl-3'-desphenyl-3'-(1-propenyl)docetaxel (Ia-P) was collected (90% conversion, 88% conversion yield) as a white solid: Mp. 131.0–132.5° C.; $^1$H NMR (CDCl$_3$, 250 MHz) δ0.57 (q, J=7.7 Hz, 6H), 0.92 (t, J=7.7 Hz, 9H), 1.05–1.11 (m, 21H), 1.20 (s, 3H), 1.23 (s, 3H), 1.32 (s, 9H), 1.69 (s, 3H), 1.73 (d, J=6.2 Hz, 3H), 1.76–1.95 (m, 1H), 2.01 (s, 3H), 2.18 (s, 3H), 2.22–2.35 (m, 2H), 2.41 (s, 3H), 2.43–2.60 (m, 1H), 3.83 (d, J=6.8 Hz, 1 H), 4.17 (d, J=8.3 Hz, 1 H), 4.31 (d, J=8.3 Hz, 1 H), 4.42–4.55 (m, 2H), 4.62 (br m, 1 H), 4.85–4.98 (m, 2H), 5.46 (dd, J=14.3, 6.2 Hz, 1 H), 5.62–5.75 (m, 2H), 6.18 (t, J=9.1 Hz, 1H), 6.47 (s, 1H), 7.49 (t, J=7.2 Hz, 2H), 7.59 (t, J=7.2 Hz, 1H), 8.11 (d, J=7.2 Hz, 2H); $^{13}$C NMR (63 MHz, CDCl$_3$) δ5.29, 6.71, 10.04, 12.50, 14.41, 17.71, 17.94, 20.85, 21.24, 22.75, 26.39, 28.18, 35.36, 37.21, 43.28, 46.73, 55.0, 58.21, 71.23, 72.24, 74.89, 75.06, 78.05, 79.5, 81.12, 84.24, 127.67, 128.64, 129.25, 130.19, 133.40, 133.53, 140.74, 155.0, 167.0, 169.25, 169.89, 171.64, 203.72.

In a similar manner, the following 7-triethylsilyl-10-O-substituted 2'-triisopropylsilyl-3'-(1-propenyl)docetaxels (I-P) were obtained in high yields:

7-Triethylsilyl-10-propanoyl-2'-triisopropylsilyl-3'-desphenyl-3'-(2-methyl-1-propenyl)docetaxel (Ib-P):

$^1$H NMR (CDCl$_3$, 250 MHz) δ0.53 (q, 6 H), 0.86 (t, 9 H), 1.09 (s, 21 H), 1.15 (s, 3H), 1.19–1.20 (m, 6 H), 1.31 (s, 9 H), 1.66 (s, 3 H), 1.73 (s, 3 H), 1.77 (s, 3 H), 1.86 (m, 1 H), 1.91 (s, 3 H), 2.34 (s, 3 H), 2.38 (s, 2 H), 2.41 (m, 1 H), 3.81 (d, J=6.6 Hz, 1 H), 4.15 (AB, $J_{AB}$=8.1 Hz, 1 H), 4.26 (AB, $J_{AB}$=8.1 Hz, 1 H), 4.41 (s, 1 H), 4.45 (m, 1 H), 4.79 (m, 1 H+NH), 4.89 (d, J=8.9 Hz, 1 H), 5.30 (d, J=7.7 Hz, 1 H), 5.65 (d, J=6.6 Hz, 1 H), 6.06 (t, 1 H), 6.47 (s, 1 H), 7.40 (t, 2 H), 7.54 (t, 1 H), 8.06 (d, 2 H).

7-Triethylsilyl-10-cyclopropanecarbonyl-2'-triisopropylsilyl-3'-desphenyl-3'-(2-methyl-1-propenyl)docetaxel (Ic-P):

$^1$H NMR (CDCl$_3$, 300 MHz) δ0.42 (m, 6 H), 0.82 (m, 9 H), 1.04 (s, 21 H), 1.12 (s, 3 H), 1.16 (s, 3 H), 1.18 (m, 2 H), 1.27 (s, 6 H), 1.62 (s, 3 H), 1.68 (bs, 5 H), 1.72 (s, 3 H), 1.84 (dt, 1 H), 1.94 (s, 3 H), 2.28 (s, 3 H), 2.32 (s, 2 H), 2.88 (ddd, 1 H), 2.50 (d, 1 H), 3.76 (d, J=6.9 Hz, 1 H), 4.11 (AB, $J_{AB}$=8.4 Hz, 1 H), 4.22 (AB, $J_{AB}$=8.4 Hz, 1 H), 4.36 (bs, 1 H), 4.39 (m, 1 H), 4.69 (m, 1 H+NH), 4.85 (d, J=9.0 Hz, 1 H), 5.25 (d, J=8.1 Hz, 1 H), 5.61 (d, J=6.6 Hz, 1 H), 5.99 (t, 1 H), 6.41 (s, 1 H), 7.37 (t, 2 H), 7.51 (t, 1 H), 8.02 (d, 2 H).

7-Triethylsilyl-10-crotonoyl-2'-triisopropylsilyl-3'-desphenyl-3'-(2-methyl-1-propenyl)docetaxel (Id-P):

$^1$H NMR (CDCl$_3$, 250 MHz) δ0.51 (q, 6 H), 0.87 (t, 9 H), 1.10 (s, 21 H), 1.17 (s, 3 H), 1.24 (s, 3 H), 1.32 (s, 9 H), 1.68 (s, 3 H), 1.74 (s, 3 H), 1.78 (s, 3 H), 1.86 (m, 1 H), 1.90 (d, 3 H), 2.03 (s, 3 H), 2.35 (s, 3 H), 2.39 (s, 2 H), 2.45 (m, 1 H), 3.84 (d, J=7.1 Hz, 1 H), 4.17 (AB, $J_{AB}$=8.3 Hz, 1 H), 4.28 (AB, $J_{AB}$=8.3 Hz, 1 H), 4.42 (d, 1 H), 4.45 (dd, J=6.4 Hz, 10.2 Hz, 1 H), 4.75 (m, 1 H+NH), 4.91 (d, J=8.5 Hz, 1 H), 5.31 (d, J=8.2 Hz, 1 H), 5.67 (d, J=7.1 Hz, 1 H), 5.92 (d, 1 H), 6.04 (t, 1 H), 6.51 (s, 1 H), 6.99 (m, 1 H), 7.42 (t, 2 H), 7.56 (t, 1 H), 8.08 (d, 2 H).

7-Triethylsilyl-10-N,N-dimethylcarbamoyl-2'-triisopropylsilyl-3'-desphenyl-3'-(2-methyl-1-propenyl)docetaxel (Ie-P):

¹H NMR (CDCl₃, 250 MHz) δ0.52 (m, 6 H), 0.86 (m, 9 H), 1.09 (s, 21 H), 1.17 (s, 3 H), 1.19 (s, 3 H), 1.31 (s, 6 H), 1.66 (s, 3 H), 1.72 (s, 3 H), 1.76 (s, 3 H), 1.85 (dt, 1 H), 2.03 (s, 3 H), 2.33 (s, 3 H), 2.38 (s, 3 H), 2.48 (ddd, 1 H), 2.91 (s, 3 H), 3.03 (s, 3 H), 3.82 (d, J=6.9 Hz, 1 H), 4.15 (AB, $J_{AB}$=8.2 Hz, 1 H), 4.25 (AB, $J_{AB}$=8.2 Hz, 1 H), 4.39 (m, 1 H), 4.41 (bs, 1 H), 4.73 (m, 1 H+NH), 4.89 (d, J=8.8 Hz, 1 H). 5.30 (d, J=8.0 Hz, 1 H), 5.65 (d, J=6.9 Hz, 1 H), 6.04 (t, 1 H), 6.38 (s, 1 H), 7.39 (t, 2 H), 7.54 (t, 1 H), 8.06 (d, 2 H).

7-Triethylsilyl-10-methoxycarbonyl-2'-triisopropylsilyl-3'-desphenyl-3'-(2-methyl-1-propenyl) docetaxel (If-P):

¹H NMR (CDCl₃, 250 MHz) δ0.52 (m, 6 H), 0.88 (m, 9 H), 1.10 (s, 21 H), 1.18 (s, 6 H), 1.32 (s, 9 H), 1.68 (s, 3 H), 1.73 (s, 3 H), 1.77 (s, 3 H), 1.83 (dt, 1 H), 2.00 (s, 3 H), 2.34 (s, 3 H), 2.38 (s, 2 H), 2.44 (ddd, 1 H), 3.79 (d, 1 H), 3.80 (s, 3 H), 4.15 (AB, $J_{AB}$=8.3 Hz, 1 H), 4.27 (AB, $J_{AB}$=8.3 Hz, 1 H), 4.41 (d, J=2.3 Hz, 1 H), 4.44 (m, 1 H), 4.74 (m, 1 H+NH), 4.90 (d, J=8.3 Hz, 1 H), 5.30 (d, J=8.2 Hz, 1 H), 5.64 (d, J=7.0 Hz, 1 H), 6.04 (t, 1 H), 6.26 (s, 1 H), 7.40 (t, 2 H), 7.55 (t, 1 H), 8.06 (d, 2 H).

7-Triethylsilyl-10-acryloyl-2'-triisopropylsilyl-3'-desphenyl-3'-(2-methyl-1-propenyl)docetaxel (Ig-P):

¹H NMR (CDCl₃, 250 MHz) δ0.51 (m, 6 H), 0.86 (m, 9 H), 1.10 (s, 21 H), 1.16 (s, 3 H), 1.24 (s, 3 H), 1.32 (s, 9 H), 1.62 (s 3 H), 1.68 (s, 3 H), 1.74 (s, 3 H), 1.78 (s, 3 H), 1.83 (m, 1 H), 2.35 (s, 2 H), 2.39 (s, 3 H), 2.42 (m, 1 H), 3.83 (d, J=7.3 Hz, 1 H), 4.16 (AB, $J_{AB}$ =8.3 Hz, 1 H), 4.28 (AB, $J_{AB}$=8.3 Hz, 1 H), 4.41 (d, J=2.1 Hz, 1 H), 4.45 (m, 1 H), 4.74 (m, 1 H+NH), 4.90 (d, J=9.4 Hz, 1 H), 5.30 (d, J=7.8 Hz, 1 H), 5.62 (d, J=7.3 Hz, 1 H), 5.88 (d, J=10.3 Hz, 1 H), 6.04 (t, 1 H), 6.17 (m, 1 H), 6.46 (m, 1 H), 6.52 (s, 1 H), 7.41 (t, 2 H), 7.56 (t, 1 H), 8.07 (d, 2 H).

EXAMPLES 22–28

3'-Desphenyl-3'-(1-alkenyl)-10-O-substituted docetaxel (I):

To a solution of 46 mg. (0.042 mmol) of the protected taxoid Ia-P in 3 mL of 1:1 mixture of acetonitrile and pyridine was added 0.5 mL of HF/pyridine (70:30). The reaction mixture was stirred at 35–40° C. for 2 hours. The reaction was quenched with 2N HCl. The mixture was extracted with EtOAc and the organic layer washed with 2N HCl and brine. After drying over MgSO₄, the crude product was purified by flash chromatography on silica gel (hexane:EtOAc=1:2) to yield 24 mg (70% yield) of the pure taxoid 3'-desphenyl-3'-(1-propenyl)-10-acetyldocetaxel (Ia) as a white solid: Mp. 152.0–155.0° C.; $[\alpha]_D$–86.7° (c, 0.15, CHCl₃); ¹H NMR (CDCl₃, 250 MHz) δ1.15 (s, 3H), 1.25 (s, 3H), 1.32 (s, 9H), 1.67 (s, 3H), 1.75 (d, J=6.3 Hz, 3H), 1.86 (br s, 4H), 2.23 (s, 3H), 2.30–2.39 (m, 2H), 2.40 (s, 3H), 2.45–2.60 (m, 1H), 3.38 (br s, 1H), 3.81 (d, J=6.9 Hz, 1H), 4.17 (d, J=8.4 Hz, 1H), 4.30–4.33 (m, 2H), 4.42 (dd, J=10.5, 6.9 Hz, 1H), 4.60 (br m, 1H), 4.90–4.98 (m, 2H), 5.53 (dd, J=16.2, 6.3 Hz, 1H), 5.67 (d, J=6.9 Hz, 1H), 5.72–5.82 (m, 1H), 6.21 (t, J=8.8 Hz, 1H), 6.30 (s, 1H), 7.52 (t, J=7.2 Hz, 2H), 7.61 (t, J=7.2 Hz, 1H), 8.11 (d, J=7.1 Hz, 2H); ¹³C NMR (63 MHz, CDCl₃) δ9.53, 14.95, 17.87, 20.84, 21.82, 22.54, 26.69, 28.18, 35.45, 35.60, 54.90, 58.62, 72.19, 73.12, 74.98, 75.61, 79.03, 79.55, 81.10, 84.41, 127.37. 128.71, 129.1, 130.19, 133.1, 133.68, 142.50, 155.50, 167.20, 170.13, 171.5, 173.40, 203.73. Anal. Calcd. for C₄₂H₅₅O₁₅N: C, 61.98; H, 6.81; N, 1.72. Found: C, 62.12; H, 6.59; N, 1.67.

In a similar manner the following 3'-Desphenyl-3'-(1-alkenyl)-10-O-substituted docetaxel (Ib-g) were obtained in high yields:

3'-Desphenyl-3'-(2-methyl-1-propenyl)-10-propanoyldocetaxel (Ib):

White solid; $[\alpha]_D^{21}$–40° (c 1.00, CHCl₃); ¹H NMR (CDCl₃, 300 MHz) δ1.08 (s, 3 H), 1.13–1.18 (m, 6 H), 1.28 (s, 9 H), 1.60 (s, 3 H), 1.69 (s, 6 H), 1.72 (m, 1 H), 1.83 (s, 3 H), 2.29 (s, 3 H), 2.31 (s, 2 H), 2.44 (m, 3 H), 3.38 (bs, OH), 3.74 (d, J=6.9 Hz, 1 H), 4.10 (AB, $J_{AB}$=8.1 Hz, 1 H), 4.13 (bs, 1 H), 4.22 (AB, $J_{AB}$=8.1 Hz, 1 H), 4.33 (dd, J=7.5 Hz, 10.1 Hz, 1 H), 4.67 (m, 1 H+NH), 4.88 (d, J=9.3 Hz, 1 H), 5.23 (d, J=8.4 Hz, 1 H), 5.59 (d, J=6.9 Hz, 1 H), 6.06 (t, 1 H), 6.24 (s, 1 H), 7.37 (t, 2 H), 7.51 (t, 2 H), 8.01 (d, 2 H); ¹³C NMR (CDCl₃, 63 MHz) δ9.0, 9.5, 14.9, 18.5, 21.8, 22.3, 25.7, 26.6, 27.5, 28.2, 35.5, 43.1, 45.6, 51.6, 55.5, 58.5, 72.1, 72.3, 73.7, 75.0, 75.4, 76.4, 76.5, 77.0, 77.5, 79.1, 79.9, 81.0, 84.3, 120.6, 128.6, 129.2, 130.1, 132.9, 133.6, 137.8, 142.4, 155.4, 166.9, 170.1, 173.0, 174.6, 203.8. HRMS (FAB, DCM/NBA), m/z: Calcd. for $C_{44}H_{59}O_{15}NH^+$, 842.3962. Found, 842.4007.

3'-Desphenyl-3'-(2-methyl-1-propenyl)-10-cyclopropanecarbonyldocetaxel (Ic):

White solid; $[\alpha]_D^{21}$–160° (c 1.00, CHCl₃); ¹H NMR (CDCl₃, 250 MHz) δ1.10 (m, 2 H), 1.14 (s, 3 H), 1.25 (s, 3 H), 1.34 (s, 9 H), 1.65 (s, 3 H), 1.71 (s, 2 H), 1.75 (s, 6 H), 1.84 (dt, 1 H), 1.88 (s, 3 H), 2.34 (s, 3 H), 2.37 (s, 2 H), 2.46 (ddd, 1 H), 2.56 (d, J=3.3 Hz, 1 H), 3.36 (d, OH), 3.78 (d, J=6.9 Hz, 1 H), 4.13 (d, J=8.4 Hz, 1 H), 4.18 (bs, 1 H), 4.27 (AB, $J_{AB}$=8.4 Hz, 1 H), 4.40 (m, 1 H), 4.72 (m, 1 H+NH), 4.93 (AB, $J_{AB}$=8.6 Hz, 1 H), 5.28 (d, J=7.6 Hz, 1 H), 5.64 (d, J=6.9 Hz, 1 H), 6.16 (t, 1 H), 6.28 (s, 1 H), 7.43 (t, 2 H), 7.56 (t, 1 H), 8.07 (d, 2 H); ¹³C NMR (CDCl₃, 63 MHz) δ9.1, 9.4, 9.5, 13.0, 14.9, 18.5, 21.9, 22.4, 25.7, 26.7, 28.2, 35.5, 35.6, 43.2, 45.6, 51.6, 58.5, 72.2, 72.3, 73.7. 75.0, 75.4. 76.5, 77.0, 77.5, 79.2, 79.7, 81.0, 84.4, 120.6, 128.6, 129.2, 130.1, 132.9, 133.6, 137.9, 142.6, 155.4, 166.9, 170.1, 175.1, 203.9; IR (neat, cm⁻¹): 3368, 2989, 2915, 1786, 1754, 1725, 1709, 1641, 1630, 1355, 1315, 1109. HRMS (FAB, DCM/NBA/NaCl), m/z: Calcd. for $C_{45}H_{59}O_{15}NNa^+$, 876.3784. Found 876.3782.

3'-Desphenyl-3'-(2-methyl-1-propenyl)-10-crotonoyldocetaxel (Id):

White solid; $[\alpha]_D^{21}$ –30° (c 1.00, CHCl₃); ¹H NMR (CDCl₃, 250 MHz) δ1.16 (s, 3 H), 1.26 (s, 3 H), 1.35 (s, 9 H), 1.67 (s, 3 H), 1.76 (s, 6 H), 1.22 (m, 1 H), 1.90 (s, 3 H), 1.92 (dd, 3 H), 2.35 (s, 3 H), 2.39 (s, 2 H), 2.49 (m, 1 H), 3.38 (bs, OH), 3.82 (d, J=6.9 Hz, 1 H), 4.10 (AB, $J_{AB}$=8.3 Hz, 1 H), 4.20 (bs, 1 H), 4.29 (AB, $J_{AB}$=8.3 Hz, 1 H), 4.45 (m, 1 H), 4.73 (m, 1 H+NH), 4.95 (d, J=7.9 Hz, 1 H), 5.30 (d, 1 H), 5.66 (d, J=6.9 Hz, 1 H), 5.95 (dd, 1 H), 6.14 (t, 1 H), 6.36 (s, 1 H), 7.03 (m, 1 H), 7.44 (t, 2 H), 7.57 (t, 1 H), 8.08 (d, 2 H); ¹³C NMR (CDCl₃, 63 MHz) δ9.5, 14.9, 18.2, 18.5, 21.9, 22.4, 25.7, 26.7, 28.2, 29.6, 35.5, 35.6, 43.2, 45.6, 51.6, 58.6, 72.2, 72.3, 73.7, 75.1, 75.3, 76.5, 77.0, 77.5, 79.2, 79.9, 81.0, 84.4, 120.6, 121.6, 128.6, 129.2, 130.1, 132.9. 133.6, 137.9, 142.6. 147.2, 155.4, 166.2, 166.9, 170.0, 173.0, 174.6, 203.8. HRMS (FAB, DCN/NBA/NaCl) m/z: Calcd. for $C_{45}H_{59}O_{15}NNa^+$, 876.3782. Found, 876.3749.

3'-Desphenyl-3'-(2-methyl-1-propenyl)-10-N,N-dimethylcarbamoyldocetaxel (Ie):

White solid; $[\alpha]_D^{21}$ –50° (c 2.00, CHCl₃); ¹H NMR (CDCl₃, 250 MHz) δ1.13 (s, 3 H), 1.23 (s, 3 H), 1.33 (s, 9 H), 1.64 (s, 3 H), 1.74 (s, 6 H), 1.85 (dt, 1 H), 1.89 (s, 3 H), 2.33 (s, 3 H), 2.36 (s, 2 H), 2.45 (ddd, 1 H), 2.93 (s, 3 H), 3.02 (s, 3 H), 3.20 (bs, Oh), 3.45 (d, OH), 3.78 (d, J=6.9 Hz, 1 H), 4.14 (AB, $J_{AB}$=8.4 Hz, 1 H), 4.18 (bs, 1 H), 4.26 (AB, $J_{AB}$=8.4 Hz, 1 H), 4.40 (dd, J=6.7 Hz, 10.2 Hz, 1 H), 4.69 (d, 1 H), 4.80 (s, NH), 4.93 (d, J=8.6 Hz, 1 H), 5.27 (d, J=7.6 Hz, 1 H), 5.62 (d, J=6.9 Hz, 1 H), 6.12 (t, 1 H), 6.23 (s, 1 H), 7.41 (t, 2 H), 7.55 (t, 1 H), 8.06 (d, 2 H); ¹³C NMR (CDCl₃, 63 MHz) δ9.3, 15.0, 18.5, 22.2, 22.3, 25.7, 26.8, 28.2, 35.3, 35.6, 36.0, 36.6, 43.1, 45.6, 51.6, 58.4, 72.3, 72.4, 73.7, 75.2, 76.2, 76.4, 76.5, 77.0, 77.5, 79.2, 81.0, 84.6, 128.6, 129.2, 130.1, 133.1, 133.6, 137.8, 142.9, 155.4, 156.1, 166.9, 170.0, 173.0, 205.6. HRMS (FAB, DCM/NBA) m/z: Calcd. for $C_{44}H_{60}O_{15}N_2Na^+$, 879.3891. Found, 879.3870.

3'-Desphenyl-3'-(2-methyl-1-propenyl)-10-methoxycarbonyldocetaxel (If):

White solid; $[\alpha]_D^{21}$–15.0° (c 2.00, CHCl₃); ¹H NMR (CDCl₃, 250 MHz) δ1.14 (s, 3 H), 1.23 (s, 3 H), 1.33 (s, 9

H), 1.68 (s, 3 H), 1.71 (s, 6 H), 1.87 (m, 1 H), 1.92 (s, 3 H), 2.34 (s, 3 H), 2.47 (d, 2 H), 2.55 (m, 1 H), 3.40 (bs, OH), 3.76 (d, J=6.9 Hz, 1 H), 3.85 (s, 3 H), 4.15 (AB, $J_{AB}$=8.3 Hz, 1 H), 4.19 (bs, 1 H), 4.28 (AB, $J_{AB}$=8.3 Hz, 1 H), 4.38 (m, 1 H), 4.72 (m, 1 H+NH), 4.93 (d, J=8.6 Hz, 1 H), 5.29 (d, J=7.8 Hz, 1 H), 5.64 (d, J=6.9 Hz, 1 H), 6.11 (s, 1 H), 6.15 (s, 1 H), 7.43 (t, 2 H), 7.56 (t, 1 H), 8.07 (d, 2 H); $^{13}C$ NMR (CDCl$_3$, 75 MHz) δ9.4, 15.0, 18.5, 21.7, 22.3, 25.7, 26.5, 28.2, 35.5, 43.1, 45.6. 51.6, 55.5. 58.6, 72.0, 72.2, 73.7, 75.0, 76.4, 76.5, 77.0, 77.2, 77.4, 78.3, 79.1, 79.9, 81.0, 84.3, 120.6, 128.6, 129.2, 130.1, 132.5, 133.6, 137.9, 143.4, 155.4, 155.7, 166.9, 170.1, 172.9. 203.9. HRMS (FAB, DCM/NBA/PPG) m/z: Calcd. for $C_{43}H_{57}O_{16}NH^+$, 844.3710. Found, 844.3755.

3'-Desphenyl-3'-trifluoromethyl-10-acetyldocetaxel (Ig):

White solid; $^1H$ NMR (250 MHz CDCl$_3$): δ1.14 (s, 3 H), 1.24 (S, 3 H), 1.30 (s, 9 H), 1.67 (s, 3 H), 1.75 (br s, 1 H), 1.92 (s, 3 H), 2.24 (s, 3 H), 2.28–2.37 (m, 5 H), 2.48–2.61 (m, 1 H), 3.46 (br d, 1 H), 3.79 (d, J=7.0 Hz, 1 H), 4.16 (d, J=8.3 Hz, 1 H), 4.30 (d, J=8.3 Hz, 1 H), 4.39 (br t, 1 H), 4.71–4.84 (m, 2 H), 4.93 (d, J=8.1Hz, 1 H), 5.24 (d, J=10.6 Hz, 1 H), 5.65 (d, J=7.0 Hz, 1 H), 6.21–6.28 (m, 2 H), 7.49 (t, J=7.4 Hz, 2 H), 7.61 (t, J=7.4 Hz, 1 H), 8.11 (d, J=7.4 Hz, 2 H), $^{13}C$ NMR (63 MHz, CDCl$_3$) δ9.57, 14.82, 20.86, 21.92, 22.35, 26.72, 27.94, 35.39, 35.58, 43.25, 45.65, 53.54, 54.03, 58.59, 68.08, 73.15, 73.32, 74.94, 75.48, 76.51, 79.01, 81.18, 81.37, 84.43, 126.24, 128.77, 129.01, 130.23, 133.38, 133.74, 141.60, 154.67, 167.16, 170.28, 171.25, 171.76, 203.54. Anal. Calc. for $C_{40}H_{50}F_3NO_{15}$:C, 57.07; H, 5.99; N, 1.66. Found: C, 56:33; H, 6.02; N, 1.69.

EXAMPLES 29–32

3'-Desphenyl-3'-(2-methylpropyl)-10-O-substituted docetaxel (Ib'):

A solution of 14 mg (0.016 mmol) of Ib in 2.0 mL of ethyl acetate was stirred under one atmosphere of hydrogen at room temperature, in the presence of palladium (10%) on activated carbon (23 mg). After 24 hours the suspension was purified by chromatography on silica gel (EtOAc) to afford 14 mg (100%) of 3'-desphenyl-3'-(2-methylpropyl)-10-propanoyldocetaxel (Ib') as a white solid: $[\alpha]_D^{21}$ –30° (c 1.00, CHCl$_3$); $^1H$ NMR (CDCl$_3$ 250 MHz) δ0.96 (d, 6 H), 1.13 (s, 3 H), 1.22–1.27 (m, 6 H), 1.30 (s, 9 H), 1.63 (s, 3 H), 1.73 (s, 3 H), 1.82 (m, 1 H), 1.88 (s, 3 H), 2.36 (s, 3 H), 2.40 (s, 2 H), 2.46 (m, 1 H), 2.49 (m, 2 H), 3.25 (bs, OH), 3.79 (d, J=7.0 Hz, 1 H), 4.09 (AB, $J_{AB}$=8.3 Hz, 1 H). 4.16 (bs, 1 H), 4.27 (AB, $J_{AB}$=8.3 Hz, 1 H), 4.38 (dd, J=6.7 Hz, 10.2 Hz, 1 H), 4.57 (d, J=9.5 Hz, NH), 4.94 (d, J=8.0 Hz, 1 H), 5.64 (d, J=7.0 Hz, 1 H), 6.13 (t, 1 H), 6.30 (s, 1 H), 7.43 (t, 2 H), 7.56 (t, 1 H), 8.08 (d, 2 H); $^{13}C$ NMR (CDCl$_3$, 63 MHz) δ9.0, 9.5, 14.9, 21.8, 21.9, 22.5, 23.2, 24.6, 26.5, 27.5, 28.1, 29.6, 35.5, 41.2, 43.1, 45.6, 51.3, 58.5, 72.1, 72.6, 73.0, 75.1, 75.4, 76.4, 76.5, 77.0, 77.5, 79.1, 79.7, 81.0, 84.4, 128.6, 129.2, 130.1, 132.9, 133.6. 142.4, 155.5, 166.9, 169.9, 173.9, 174.6, 203.8. HRMS (FAB, DCM/NBA) m/z: Calcd. for $C_{44}H_{61}O_{15}NH^+$, 844.4119. Found, 844.4157.

In the same manner, the following 3'-desphenyl-3'-(2-methylpropyl)-10-O-substituted docetaxel (Ic'-f') were obtained in quantitative yields:

3'-Desphenyl-3'-(2-methylpropyl)-10-cyclopropanecarbonyldocetaxel (Ic'):

White solid; $[\alpha]_D^{21}$–30° (c 1.00, CHCl$_3$, 250 MHz) δ0.96 (d, 6 H), 1.09 (m, 2 H), 1.14 (s, 3 H), 1.24 (s, 3 H), 1.30 (s, 9 H), 1.62–1.70 (m, 4 H), 1.66 (s, 3 H), 1.73 (m, 1 H), 1.88 (s, 3 H), 2.36 (s, 3 H), 2.39 (s, 1 H), 2.48 (ddd, 1 H), 2.50 (d, 1 H), 3.20 (d, OH), 3.78 (d, J=6.9 Hz, 1 H), 4.16 (AB, $J_{AB}$=8.3 Hz, 1 H), 4.20 (bs, 1 H), 4.27 (AB, $J_{AB}$=8.3 Hz, 1 H), 4.40 (m, 1 H), 4.55 (d, NH), 4.93 (d, J=8.1 Hz, 1 H), 5.64 (d, J=7.0 Hz, 1 H), 6.14 (t, 1 H), 6.29 (s, 1 H), 7.43 (t, 2 H), 7.56 (t, 1 H), 8.09 (d, 2 H);, $^3C$ (CDCl$_3$, 63 MHz) δ9.1, 9.4, 9.5, 13.0, 14.9, 21.9, 22.0, 22.5, 23.2, 24.7, 26.6, 28.1, 35.4, 35.5, 41.2, 43.1, 45.6, 51.3, 58.5, 72.2, 72.7, 72.9, 75.1, 75.4, 76.5, 77.0. 77.5. 79.2, 79.7, 81.0, 84.4, 128.6, 129.2, 130.2, 132.9, 133.6, 142.6, 155.5, 166.9, 169.9, 173.9, 175.1, 203.9. HRMS (FAB, DCM/NBC/NaCl), m/z: Calcd. for $C_{45}H_{61}O_{15}NNa^+$, 878.3938. Found, 878.3926.

3'-Desphenyl-3'-(2-methylpropyl)-10-N,N-dimethylcarbamoyldocetaxel (Ie'):

White solid; $[\alpha]_D^{21}$–80° (c 2.00, CHCl$_3$), $^1H$ NMR (CDCl$_3$, 250 MHz) δ0.95 (d, 6 H), 1.14 (s, 3 H), 1.23 (s, 3 H), 1.29 (s, 9 H), 1.66 (s, 3 H), 1.68 (m, 2 H), 1.82 (m, 1 H), 1.90 (s, 3 H), 2.36 (s, 3 H), 2.39 (s, 2 H), 2.50 (m, 1 H), 2.95 (s, 3 H), 3.03 (s, 3 H), 3.22 (d, OH), 3.78 (d, J=7.0 Hz, 1 H), 4.10 (AB, $J_{AB}$=8.3 Hz, 1 H), 4.16 (bs, 1 H), 4.27 (AB, $J_{AB}$=8.3 Hz, 1 H), 4.41 (dd, J=6.5 Hz, 10.2 Hz, 1 H), 4.56 (d, NH), 4.95 (d, J=8.1 Hz, 1 H), 5.63 (d, J=7.0 Hz, 1 H), 6.14 (t, 1 H), 6.24 (s, 1 H), 7.42 (t, 2 H), 7.56 (t, 1 H), 8.08 (d, 2 H); $^{13}C$ NMR (CDCl$_3$, 75 MHz) δ9.8, 15.3, 22.3. 22.7, 22.9, 23.6, 25.1, 27.2, 28.5, 35.8, 36.0, 36.4, 37.0, 41.6, 43.6, 46.0. 51.7, 58.9, 72.8, 73.1, 75.7, 76.6, 76.8, 76.9, 77.1, 77.4, 77.6, 77.8, 79.6, 80.0, 81.5, 85.0, 128.7, 129.0, 129.7, 130.6, 133.6, 133.9, 143.3, 155.9, 156.5, 167.3, 170.3, 174.3, 206.0. HRMS (FAB) m/z: Calcd. for $C_{44}H_{62}O_{15}N_2Na^+$, 881.4074. Found, 881.4047.

3'-Desphenyl-3'-(2-methylpropyl)-10-methoxycarbonyldocetaxel (If'):

White solid; $[\alpha]_D^{21}$–70° (c 1.00, CHCl$_3$); $^1H$ NMR (CDCl$_3$, 250 MHz) δ0.96 (d, 6 H), 1.14 (s, 3 H), 1.23 (s, 3 H), 1.30 (s, 9 H), 1.66 (s, 2 H), 1.69 (s, 3 H), 1.84 /(m, 1 H), 1.92 (s, 3 H), 2.37 (s, 3 H), 2.47 (s, 2 H), 2.55 (m, 1 H), 3.24 (d, OH), 3.77 (d, J=6.8 Hz, 1 H), 3.86 (s, 3 H), 4.16 (AB, $J_{AB}$=8.2 Hz, 1 H), 4.17 (bs, 1 H), 4.28 (AB, $J_{AB}$=8.2 Hz, 1 H), 4.40 (dd, 1 H), 4.56 (d, J=9.3 Hz, NH), 4.94 (d, J=8.0 Hz, 1 H), 5.65 (d, J=7.0 Hz, 1 H), 6.11 (s, 1 H), 6.18 (t, 1 H), 7.43 (t, 2 H), 7.56 (t, 1 H), 8.09 (d, 2 H); $^{13}C$ NMR (CDCl$_3$, 75 MHz) δ9.5, 15.0, 21.8, 22.5, 23.2, 24.7, 26.5, 28.1, 35.5, 35.6, 41.2, 43.0, 45.5, 51.3, 55.5, 58.5, 72.0, 72.6, 73.0, 75.0, 76.5, 77.0, 77.5, 78.3, 79.1, 79.7. 81.0, 84.3, 128.6, 129.2, 130.2, 132.5, 133.6, 143.5, 155.5, 155.7, 166.9, 170.0, 173.9, 204.0. HRMS (FAB, DCM/NBA) m/z: Calcd. for $C_{43}H_{59}O_{16}NH^+$, 846.3912. Found, 846.3942.

EXAMPLE 33

Taxoid Ia and Ig were evaluated for tumor growth inhibitory activities against human tumor cell line, A121 (ovarian carcinoma), A549 (non-small cell lung carcinoma), HT-29 (colon carcinoma), MCF7 (mammary carcinoma) or MCF7-R (mammary carcinoma cells 180-fold resistant to adriamycin), after 72 h drug exposure according to the literature method (see below). Results are shown in Table 1. Lower numbers indicate higher potency. Paclitaxel, docetaxel, and RAH-1 (see above) were also used for comparison. The data represent the mean values of at least three separate experiments. Lower numbers indicate greater activity.

TABLE 1

| Taxoid | A121[a] (ovarian) | A549[a] (NSCLC) | HT-29[a] (colon) | MCF7[a] (breast) | MCF7-R[a] |
|---|---|---|---|---|---|
| Paclitaxel | 6.1 | 3.6 | 3.2 | 1.7 | 300 |
| Docetaxel | 1.2 | 1.0 | 1.2 | 1.0 | 235 |
| RAH-1 | 1.4 | 0.45 | 0.96 | 0.54 | 113 |
| Ia | 0.90 | 0.54 | 0.76 | 0.51 | 14 |
| Ig | 0.37 | 0.25 | 0.4 | 0.25 | 17 |

[a]The concentration of compound which inhibits 50% (IC$_{50}$, nM) of the growth of human tumor cell line.

Assessment of cell growth inhibition was determined according to the methods of Skehan et al., *J. Nat. Cancer Inst.* 1990, 82, 1107. Briefly, cells were plated between 400 and 1200 cells/well in 96 well plates and incubated at 37° C. for 15–18 h prior to drug addition to allow attachment of cells. Compounds tested were solubilized in 100% DMSO and further diluted in RPMI-1640 containing 10 mM HEPES. Each cell line was treated with 10 concentrations of compounds (5 log range). After a 72 h incubation, 100 mL of ice-cold 50% TCA was added to each well and incubated for 1 h at 4° C. Plates were then washed 5 times with tap water to remove TCA, low-molecular-weight metabolites and serum proteins. Sulforhodamine B (SRB) (0.4%, 50 mL) was added to each well. Following a 5 min incubation at room temperature, plates were rinsed 5 times with 0.1% acetic acid and air dried. Bound dye was solubilized with 10 mM Tris Base (pH 10.5) for 5 min on a gyratory shaker. Optical density was measured at 570 nm.

Data were fit with the Sigmoid-Emax concentration-effect model (see Holford, N. H. G.; Scheiner, L. B., "Understanding the dose-effect relationship: Clinical applications of pharmaco-kinetic-pharmacodynamic models.", *Clin. Pharmiacokin.* 1981, 6, 429–453) with non-linear regression, weighted by the reciprocal of the square of the predicted response. The fitting software was developed by the Roswell Park Cancer Institute with Microsoft FORTRAN, and uses the Marquardt algorithm (see Marquardt, D. W., "An algorithm for least squares estimation of nonlinear parameters", *J. Soc. Ind. Appl. Math.* 1963, 11, 431–441) as adopted by Nash (see Nash, J. C., "Compact numerical method for computers: Linear algebra and function minimization", John Wiley & Sons, New York, 1979) for the non-linear regression. The concentration of drug which resulted in 50% growth inhibition ($IC_{50}$) was calculated.

Since the new taxoids of this invention are unique in that these taxoids possess extremely high activities against drug-resistant human breast cancer cells MCF7-R (two orders of magnitude better than paclitaxel and docetaxel), the activities of these taxoids other than Ia and Ig were evaluated against human breast cancer cells (MCF7) (sensitive) and resistant cells (MCF7-R) (resistant) in the same manner as described above. Results are summarized in TABLE 2.

TABLE 2

| Taxoid | $R^1$ | $R^5$ | MCF7 $IC_{50}$ (nM) | MCF7-R $IC_{50}$ (nM) |
|---|---|---|---|---|
| Ib | 2-methyl-1-propenyl | $COCH_2CH_3$ | 0.21 | 2.16 |
| Ib' | 2-methylpropyl | $COCH_2CH_3$ | 0.35 | 2.84 |
| Ic | 2-methyl-1-propenyl | cyclopropyl-carbonyl | 0.20 | 2.11 |
| Ic' | 2-methylpropyl | cyclopropyl-carbonyl | 0.51 | 4.33 |
| Id | 2-methyl-1-propenyl | crotonoyl | 0.26 | 3.35 |
| Ie | 2-methyl-1-propenyl | $CON(CH_3)_2$ | 0.13 | 4.91 |
| Ie' | 2-methylpropyl | $CON(CH_3)_2$ | 0.36 | 5.80 |
| If | 2-methyl-1-propenyl | $CO_2CH_3$ | 0.14 | 5.25 |
| If' | 2-methylpropyl | $CO_2CH_3$ | 0.48 | 6.35 |

I claim:
1. A taxoid of the formula (I):

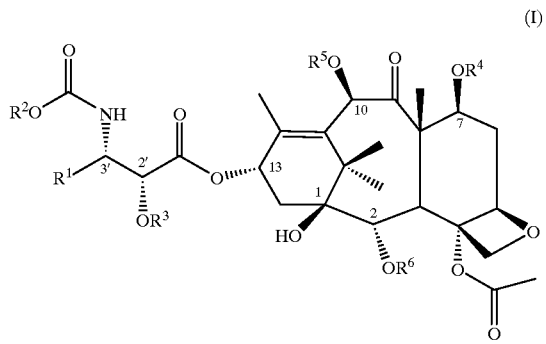

wherein
   $R^1$ is an unsubstituted or alkyl-substituted $C_3$ alkyl or $C_3$ alkenyl radical, wherein the $C_3$ alkenyl radical is not a 1-propenyl radical;
   $R^2$ is a $C_3$–$C_5$ branched alkyl radical;
   $R^3$ and $R^4$ are hydrogen;
   $R^5$ is an acyl radical other than an acetyl radical, or an alkoxycarbonyl or carbamoyl radical; and
   $R^6$ is an acyl radical.

2. A taxoid according to claim 1 wherein:
   $R^1$ is propyl, 2-methyl-1-propenyl, 1-methyl-1-propenyl, 2-methyl propyl, 1-methylpropyl, cyclopropyl, or cyclopropylmethyl radical;
   $R^2$ is selected from isopropyl, cyclopropyl, isobutyl, sec-butyl, 2-methylpropyl, 3-methylpropyl, tert-butyl, cyclobutyl, cyclopentyl, 1-ethylpropyl, or 1,1-dimethylpropyl radicals;
   $R^5$ is selected from $C_3$–$C_6$ acyl, $C_1$–$C_6$ alkoxycarbonyl, $C_1$–$C_6$ N-alkylcarbamoyl, or $C_1$–$C_6$ N,N-dialkylcarbamoyl radicals;
   $R^6$ is selected from benzoyl, fluorobenzoyl, chlorobenzoyl, azidobenzoyl, cyclohexanecarbonyl, acryloyl, crotonoyl, 1-methylacryloyl, 2-methyl-2-butenoyl, or 3-methyl-3-butenoyl radicals; and
   $R^3$ and $R^4$ are hydrogen.

3. A taxoid according to claim 1 wherein:
   $R^1$ is propyl, 2-methyl-1-propenyl, 1-methyl-1-propenyl, 2-methylpropyl, 1-methylpropyl, cyclopropyl, or cyclopropyl methyl radical;
   $R^2$ is a tert-butyl radical;
   $R^5$ is selected from triethoxycarbonyl, trifluoroacetyl, propanoyl, cyclopropanecarbonyl, acryloyl, crotonoyl, 3,3-dimethylacryloyl, N-methylcarbamoyl, N-ethylcarbamoyl, N-propylcarbamoyl, N-isopropylcarbamoyl, N-butylcarbamoyl, N-pentylcarbamoyl, N-hexylcarbamoyl, N,N-dimethylcarbamoyl, N, N-diethylcarbamoyl, N,N-dipropylcarbamoyl, N,N-dibutylcarbamoyl, pyrrolidine-N-carbonyl, piperidine-N-carbonyl, morpholine-N-carbonyl, methoxycarbonyl, ethoxylcarbonyl, propoxylcarbonyl, butoxycarbonyl, cyclopentanecarbonyl, or cyclohexanecarbonyl radicals; and
   $R^6$ is a benzoyl radical.

4. A taxoid according to claim 1 wherein:
   $R^1$ is propyl, 2-methyl-1-propenyl, 2-methylpropyl, cyclopropyl, or cyclopropylmethyl radical;
   $R^2$ is a tert-butyl radical;
   $R^3$ is hydrogen;
   $R^4$ is hydrogen;

$R^5$ is selected from propanoyl, cyclopropanecarbonyl, acryloyl, crotonoyl, 3,3-dimethylacryloyl, N-methylcarbamoyl, N-ethylcarbamoyl, N,N-dimethylcarbamoyl, N,N-diethylcarbamoyl, pyrrolidine-N-carbonyl, piperidine-N-carbonyl, morpholine-N-carbonyl, methoxycarbonyl, ethoxylcarbonyl, propoxylcarbonyl, butoxycarbonyl, cyclopentanecarbonyl, or cyclohexanecarbonyl radicals; and $R^6$ is a benzoyl radical.

5. A taxoid according to claim 1 wherein:

$R^1$ is a 2-methyl-1-propenyl, or 2-methylpropyl radical;

$R^2$ is a tert-butyl radical;

$R^3$ is hydrogen;

$R^4$ is hydrogen;

$R^5$ is selected from propanoyl, cyclopropanecarbonyl, crotonoyl, N,N-dimethylcarbamoyl, methoxycarbonyl, or acryloyl radicals; and $R^1$ is a benzoyl radical.

6. A pharmaceutical composition having antineoplastic activity comprising the compound of claim 1 and a physiologically acceptable carrier therefor.

7. A method for treating tumors which comprises administrating to a patient an effective antitumor amount of the compound of claim 1.

8. A method according to claim 7 wherein said treatment comprises treating tumors selected from the group consisting of leukemia, melanoma, breast, non-small cell lung, ovarian, and colon cancers.

9. A taxoid according to claim 1 wherein $R^1$ is a 2-methyl-1-propenyl or 2-methylpropyl radical, $R^5$ is an acyl radical other than an acetyl radical, alkoxycarbonyl, or N,N-dialkylcarbamoyl group, and $R^2$, $R^3$, $R^4$, and $R^6$ are defined as in claim 1.

10. A method for preparing a taxoid according to claim 1 comprising coupling baccatins of formula (II)

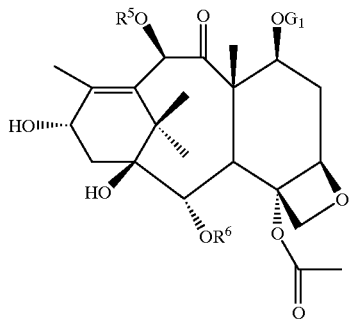

(II)

wherein $G_1$ represents a hydroxyl protecting group, and $R^5$ and $R^6$ are defined in claim 1, with the β-lactams of formula (III)

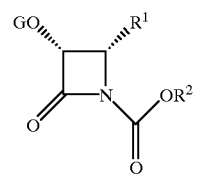

(III)

wherein G is a hydroxyl protecting group and $R^1$ and $R^2$ are defined in claim 1, in the presence of a base.

11. The taxoid according to claim 1, wherein:

$R^1$ is a 2-methyl-1-propenyl or 2-methylpropyl radical; and $R^2$, $R^3$, $R^4$, $R^5$, and $R^6$ are defined as in claim 1.

12. The taxoid according to claim 1, wherein:

$R^1$, $R^2$, $R^3$, $R^4$, and $R^6$ are defined as in claim 1; and $R^5$ is an acyl radical other than an acetyl radical, alkoxycarbonyl, or N,N-dialkylcarbamoyl group.

13. The taxoid according to claim 1, wherein the alkyl substituent of the $C_3$ alkyl or C3 alkenyl radical is a methyl radical.

14. A taxoid of the formula (I):

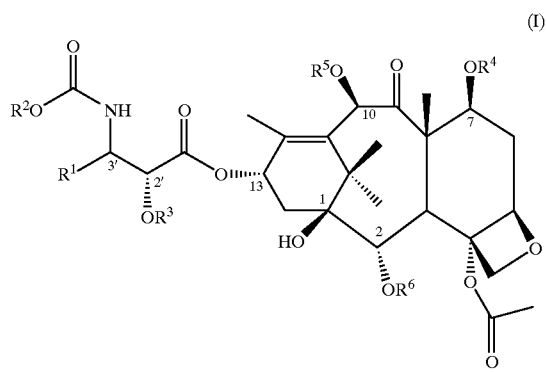

(I)

wherein $R^1$ is a trifluoromethyl radical;

$R^2$ is a $C_3$–$C_5$ branched alkyl radical;

$R^3$ and $R^4$ are independently selected from hydrogen and hydroxyl protecting groups including functional groups which increase the water solubility of the taxoid antitumor agent;

$R^5$ is hydrogen or an acyl, alkoxycarbonyl, or carbamoyl radical; and $R^6$ is an acyl radical.

15. A method for treating tumors which comprises administering to a patient an effective amount of a taxoid of claim 14.

16. A pharmaceutical composition having antineoplastic activity comprising a taxoid of claim 14 and a physiologically acceptable carrier.

* * * * *

UNITED STATES PATENT AND TRADEMARK OFFICE
CERTIFICATE OF CORRECTION

PATENT NO. : 6,100,411
DATED : August 8, 2000
INVENTOR(S) : Iwao Ojima

It is certified that error appears in the above-identified patent and that said Letters Patent is hereby corrected as shown below:

Claim 2, column 20,
Line 30, "2-methyl propyl" should read -- 2-methylpropyl --.

Claim 3, column 20,
Line 47, "cyclopropyl methyl" should read -- cyclopropylmethyl --.

Claim 5, column 21,
Line 20, "$R^1$" should read -- $R^6$ --.

Claim 13, column 22,
Line 21, "C3" should read -- $C_3$ --.

Signed and Sealed this

Thirtieth Day of October, 2001

Attest:

NICHOLAS P. GODICI
Attesting Officer   Acting Director of the United States Patent and Trademark Office